| United States Patent [19] | [11] Patent Number: 5,049,395 |
|---|---|
| Chang | [45] Date of Patent: Sep. 17, 1991 |

[54] CONTROLLED RELEASE VEHICLE

[75] Inventor: An-Cheng Chang, Nashua, N.H.

[73] Assignee: Micro Vesicular Systems, Inc., Nashua, N.H.

[21] Appl. No.: 521,086

[22] Filed: May 9, 1990

Related U.S. Application Data

[63] Continuation-in-part of Ser. No. 320,944, Mar. 9, 1989, Pat. No. 4,959,341, and a continuation-in-part of Ser. No. 371,210, Jun. 26, 1989, Pat. No. 4,944,734, and a continuation-in-part of Ser. No. 490,356, Mar. 8, 1990, Pat. No. 4,952,550.

[51] Int. Cl.$^5$ .............. A61K 9/16; A61K 9/24; A61K 9/50
[52] U.S. Cl. .................... 424/494; 424/473
[58] Field of Search ............. 424/488, 494, 461, 480, 424/473; 435/179

[56] References Cited

U.S. PATENT DOCUMENTS

| 3,969,280 | 7/1976 | Sayce et al. | 252/522 |
|---|---|---|---|
| 3,986,510 | 10/1976 | Higuchi et al. | 128/260 |
| 4,090,013 | 5/1978 | Ganslaw et al. | 526/15 |
| 4,160,063 | 7/1979 | Titus | 428/389 |
| 4,486,335 | 12/1984 | Majewicz | 252/315.3 |
| 4,610,678 | 9/1986 | Weisman et al. | 604/368 |
| 4,786,415 | 11/1988 | Shibata et al. | 210/635 |
| 4,812,486 | 3/1989 | Hosokawa et al. | 521/139 |
| 4,826,880 | 5/1989 | Lesniak et al. | 521/53 |

FOREIGN PATENT DOCUMENTS 1152483 8/1983 Canada.

OTHER PUBLICATIONS

Kyoritsu Yuki Kogyo, Computerized Abstract.
Diacel Chem. Ind. KK, Computerized Abstract.
Borrmeiste et al., Computerized Abstract.

Primary Examiner—Thurman K. Page
Assistant Examiner—G. S. Kishore
Attorney, Agent, or Firm—Lahive & Cockfield

[57] ABSTRACT

A new controlled release vehicle which acts by breakdown of the entrapping material upon hydration has been developed. The preferred release vehicle is made of a carboxylated cellulose, e.g., carboxymethylcellulose, which is treated with a cross-linking agent such as aluminum ions and, preferably, a hydrophobicity agent such as acetic acid. The vehicle is broken down by a release agent, e.g., cellulase, which may be coated on the vehicle together with a coating agent, e.g., hydroxypropylcellulose. The vehicle is dried, entrapping the molecular to be entrapped, e.g., an enzyme, and hydration activates the cellulase which breaks down the carboxymethylcellulose, releasing the entrapped molecular.

19 Claims, No Drawings

CONTROLLED RELEASE VEHICLE

REFERENCE TO RELATED APPLICATIONS

The present application is a continuation-in-part of U.S. patent application Ser. No. 320,944 U.S. Pat. No. 4,956,341, issued Sept. 25, 1990, entitled "Biodegradable Superabsorbing Sponge," filed Mar. 9, 1989, U.S. patent application Ser. No. 371,210, U.S. Pat. No. 4,944,734, issued July 31, 1990, entitled "Biodegradable Incontinence Device," filed June 26, 1989, and U.S. patent application Ser. No. 490,356, U.S. Pat. No. 4,952,550, issued Aug. 28, 1990, entitled "Particulate Absorbent Material," filed Mar. 8, 1990. The disclosures of all three patents are incorporated herein by reference.

BACKGROUND OF THE INVENTION

The present invention relates to controlled release systems which release entrapped molecules over time upon hydration. More particularly, the present invention relates to controlled release vehicles and methods of their manufacture by using a cellulose-based system. Release of the entrapped molecule is carried out by degradation of the cellulose using a release agent such as an enzyme which degrades the cellulose. These controlled release vehicles can be stored in dry or dehydrated form so that they are not activated until hydration. In certain instances, the entrapping vehicle is distinct from the release agent, e.g., the cellulose degrading enzyme can be carried on a separate particle or be added later to activate the system.

Controlled release vehicles have been available for many years. There are two general types of controlled release vehicles: those that release the entrapped material by some type of sieving mechanism through a series of pores, and those that release the materials upon degradation of the vehicle. The first class of controlled release vehicles include microcapsules and other vehicles which have a porous shell surrounding a substantially amorphous center. Release of the entrapped molecules takes place via diffusion or flow through the pores perforating the shell until they are released. Control of release is achieved by modification of the pore size and shell thickness so as to limit the particle size which can traverse the membrane easily, thereby controlling the time of traverse.

The second class of controlled release vehicles are those that degrade to release the material. Although some microcapsules also belong to this category, this class is primarily concerned with vehicles such as liposomes or some other type of biodegradable material which can be cleaved by a molecule, e.g., an enzyme. The vehicles are particularly useful for injection or ingestion where enzymes in the blood stream, the implantation site, or the gastrointestinal tract can degrade the vehicle in the host. For example, most phospholipids are susceptible to phospholipases and other enzymes which attack lipids. Other systems are made of materials such as alginates or gelatin which are degraded by sugar-reactive enzymes or proteases. These degradable vehicles may entrap the molecule of interest but, more normally, the molecule to be released is bound, either chemically or ionically, to the material forming the vehicle. Upon break-up of the vehicles, the bound material is released from the vehicle material, and the controlled release is achieved by the strength of the bond and the location where the material is bound. If a shell-like vehicle is used, e.g., a microcapsule or unilamellar lipid vesicle, degradation of the wall structure will cause immediate release of all the material entrapped inside. Controlled release in that circumstance can only be achieved by controlling the duration of the breakdown. In order to achieve true controlled release, a mixture of a variety of vehicles having different breakdown rates can be used in the same sample.

While either the shell-type or the breakdown vehicle could be used in certain circumstances, each type of vehicle has attendant problems. The shell-type vehicle normally requires an aqueous environment since such vehicles are susceptible to degradation upon drying. While certain of the breakdown-type vehicles can be used in a dry form, they normally require a host or some other added material which breaks down the structure to operate. Further, the breakdown-type vehicle is normally not easy to control in terms of release rate.

Accordingly, an object of the invention is to provide a controlled release vehicle which can be used in a dehydrated form and is activated only upon hydration.

Another object of the invention is to provide a method of producing a controlled release vehicle which can be used in dehydrated form.

A further object of the invention is to provide a system which has a vehicle-type carrier and a separate release agent in dehydrated form which, upon hydration, degrades the vehicle and releases an entrapped molecule.

A still further object of the invention is to provide a vehicle which traps and releases the enzymes upon hydration.

These and other objects and features of the invention will apparent from the following description.

SUMMARY OF THE INVENTION

The present invention features a substantially dry system for entrapping molecules which provides release of the entrapped molecule upon hydration. The invention further features an enzyme or protein carrier in dehydrated form which can release the enzyme or protein upon hydration. A still further feature of the invention is a method of manufacturing the system of the invention.

The invention is based on the ability of certain materials, preferably modified cellulosic materials, to entrap a variety of molecules. These cellulosic materials can be totally or partially dehydrated while retaining a substantial portion of the entrapped material. Upon rehydration, these vehicles will still retain the materials until degraded. The preferred cellulosic materials for use in the invention are partially cross-linked carboxylated cellulosic compounds. Preferred cellulosic compounds include carboxymethylcellulose, particularly a carboxymethylcellulose partially cross-linked with aluminum or ferric ions. These materials are preferably treated with a hydrophobicity agent, e.g., one selected from the group consisting of acetic acid, proprionic acid, butyric acid, isobutyric acid, succinic acid, adipic acid, phthalic acid, citric acid, and salts, chlorides, anhydrides, and mixtures of the foregoing. Preferred aluminum compounds to provide the cross-linking include aluminum acetate, aluminum isopropoxide, aluminum hydroxide, and mixtures thereof. In addition, ferric salts such as ferric chloride could be used. Although a large variety of carboxymethylcellulose materials could be used, preferably the carboxymethylcellulose has a Degree of Substitution ("DS") of 0.5 or greater, most preferably 0.7 or greater.

Carboxymethylcellulose compounds with this DS value have such a substantial number of sites available for cross-linking that total cross-linking would yield an unworkable material so only partial cross-linking is used.

The cellulosic compound is used to form the entrapping vehicle which entraps the molecule which will be released. Preferably, the molecule is capable of being carried in an aqueous solution, whereby the cellulosic compound, before cross-linking, is soaked with a solution of the molecule to be entrapped. After this soaking, cross-linking and preferably treatment with the hydrophobicity agent is allowed to occur, thereby partially entrapping the molecule. At this stage, the swollen cellulosic compound having the molecule to be entrapped therein is normally allowed to dry.

After the first drying, a coating agent may be used to form a barrier about the entrapping vehicle. Preferably, the coating agent is also cellulose-based so that it can be degraded along with the entrapping vehicle. The preferred coating agent is hydroxypropylcellulose but other cellulose compounds, primarily the hydroxyalkylcellulose family, is preferred. The coating agent is normally added by soaking the pre-dried entrapment vesicles in a diluted solution of the coating agent. Preferably, the soaking agent is dissolved in an alcohol such as isopropyl alcohol for this soaking step.

The system of the invention relies on a release agent which is inactive or quiescent in a dry state but which can degrade both the coating agent (if present) and the entrapping vehicle itself upon hydration. Preferably, the release agent is an enzyme selected from the group consisting of cellulase, hemicellulase, and related cellulose degrading enzymes. One important factor about the release agent is that it should not degrade the entrapped molecule except to the extent necessary for activation of the entrapped molecule. In one preferred embodiment of the invention, the release agent is added to the solution containing the coating agent and accordingly is coated on the surface of the entrapping vehicle together with the coating agent. Since the barrier formed by the coating agent is dried after it is allowed to coat the entrapping vehicle, the release agent does not get a chance to degrade the entrapping agent until it is rehydrated. In another preferred embodiment, the release agent is carried by a separate particle. Most preferably, this separate particle is substantially identical to the entrapping vehicle, including having a barrier film of coating agent, except it does not contain the entrapped molecule. In still another embodiment of the invention, the release agent is added as a powder or other dry, dehydrated form.

Other embodiments of the invention, and further features, will be apparent from the following description.

DETAILED DESCRIPTION OF THE INVENTION

The present invention features both a system for providing sustaining release of an entrapped molecule and a method of forming the sustained release system. This system, which is completely biodegradable, can be used either in vivo or in vitro. The system is self-contained in a dehydrated state and the addition of any aqueous-based solvent, e.g., water, urine, or saline, can activate the system and provide controlled release of the entrapped molecule. The system is flexible in that a number of different factors can be controlled to provide the desired release characteristics.

Briefly, the system consists of a carboxylated cellulosic compound such as carboxymethylcellulose which has been partially cross-linked and preferably is treated with a hydrophobicity agent. A carboxymethylcellulose with a high DS value, preferably above 0.5, is most useful. Partial cross-linking is normally achieved using a multivalent metal ion such as aluminum to provide a stable, hydratable structure. A hydrophobicity agent such as a monobasic or dibasic acid, or a salt, anhydride, or chloride thereof, may be added to provide further stability. The preferred hydrophobicity agents are acetic proprionic, butyric, isobutyric, adipic, phthalic, citric, and succinic acids and their salts, anhydride, and chlorides. While monobasic acids are preferred, certain polybasic acids can also be used. Further details concerning the preferred cross-linking agents and hydrophobicity agents can be found in U.S. Pat. No. 4,952,550 previously incorporated by reference.

The molecule to be entrapped is normally taken up into the cellulose material by incorporating the molecule in an aqueous solution and allowing the cellulose material to soak and swell in the solution. Most preferably, swelling takes place before the cross-linking or treatment with the hydrophobicity agent. Once the treatments with both hydrophobicity agent and cross-linker are finished, the molecule is normally dried.

After drying, the cellulose material containing the entrapped molecule is normally treated with a coating agent which forms a barrier about the cellulose compound, further entrapping the molecule to be released. This coating agent should also be able to be degraded by the release agent. Preferably, the coating agent is hydroxypropylcellulose or a related compound. The hydroxypropylcellulose is normally dissolved in isopropyl alcohol and coated on the cellulose particle by immersion of the vehicle in the solution.

A release agent, normally in the form of an enzyme which degrades both the coating and the cellulose vehicle, is a necessary part of the system. Preferably, an enzyme such as cellulase or hemicellulase is used as this release agent. Normally, the cellulase is included in the isopropyl alcohol solution used for the hydroxypropylcellulose coating, thereby coating the cellulase on the outside of the carboxymethylcellulose-based particle. However, the enzyme may be on a separate particle which does not include the entrapped material, may be entrapped in the vehicle, or may be added in some dry form.

The types of molecules which may be entrapped using this process range greatly in size. Small molecules such as drugs (molecular weight approximately 100–300 daltons) may be used as may large enzymes and other molecules (molecular weight 30,000 daltons and greater). This broad range of uses is very different from the porous entrapment systems which have limited ranges of effectiveness in terms of molecule size which can be entrapped.

The following non-limiting Examples will help further explain the invention and its uses.

EXAMPLE 1

In this Example, a series of tests were run using a low molecular weight dye, Brilliant Blue R (molecular weight 825 daltons), to show the efficacy of the present invention for small molecules.

First, 10 g of carboxymethylcellulose (CMC 7HC from Aqualon Company) having a DS of 0.7 was mixed with 5 g of isopropanol. A NaCl solution (90 mg NaCl/g CMC) (35 ml) containing 8 mg of Brilliant Blue R (Aldrich Co.) was added to the carboxymethylcellulose over two minutes. The carboxymethylcellulose particles swell during this time. After ten minutes, the initial solution was decanted and 35 ml of a solution containing 90 mg NaCl/g of carboxymethylcellulose was added. The solution also contained the cross-linking agent, aluminum acetate:borate, and the hydrophobicity agent, acetic acid. This solution was added over the same two minute period with stirring. As is shown in Table I, various concentrations of the aluminum acetate:borate cross-linker and the acetic acid hydrophobicity agent were tested.

The swollen particles were then dried at room temperature overnight.

After drying, the particles were coated using a solution containing hydroxypropylcellulose coating agent and cellulase as a release agent in isopropanol. Approximately 0.6 ml of the isopropanol solution was tested, each sample containing a different concentration of hydroxypropylcellulose and cellulase (see Table I) The hydroxypropylcellulose (type EF NF) was obtained from Aqualon Company while the cellulase was obtained from Sigma Company (No. C-0901). The isopropanol solution was mixed with one g of the carboxymethylcellulose containing the Brilliant Blue R then the resulting material was dried by blowing with cool air. Within about twenty minutes, the material was dry.

The following release studies were used to determine whether the cellulose releases the dye upon hydration. Fifty mg samples of each test material was added to a test tube containing 10 g of water. Before analysis, the whole solution was shaken upside-down twice to differentiate the enzyme triggered release mechanism from simple diffusion controlled processes. The absorbence was measured at 585 nm in a Turner spectrophotometer. Table I shows the results of these experiments.

TABLE I

Concentration effect of hydroxypropylcellulose (HPC) on release of Brilliant Blue R
CMC + Dye = 50 mg
OD585 nm
H$_2$O - 10 g

| No. | Al (mg/g)/ Acetic Acid (mg/g) | HPC (mg/g) | Enzyme (mg/g) | 3 hr/ OD | 6 hr/ OD | 24 hr/ OD |
| --- | --- | --- | --- | --- | --- | --- |
| 1 | 10/20 | 12 | 0 | 0.030 | 0.050 | 0.060 |
| 2 | 20/40 | 12 | 0 | 0.020 | 0.042 | 0.050 |
| 3 | 30/60 | 12 | 0 | 0.095 | 0.132 | 0.142 |
| 4 | 10/20 | 12 | 2.5 | 0.110 | 0.130 | 0.120 |
| 5 | 20/40 | 12 | 2.5 | 0.115 | 0.142 | 0.140 |
| 6 | 30/60 | 12 | 2.5 | 0.080 | 0.120 | 0.145 |
| 7 | 10/20 | 18 | 0 | 0.020 | 0.030 | 0.032 |
| 8 | 20/40 | 18 | 0 | 0.020 | 0.045 | 0.050 |
| 9 | 30/60 | 18 | 0 | 0.080 | 0.110 | 0.133 |
| 10 | 10/20 | 18 | 2.5 | 0.115 | 0.130 | 0.120 |
| 11 | 20/40 | 18 | 2.5 | 0.117 | 0.140 | 0.135 |
| 12 | 30/60 | 18 | 2.5 | 0.092 | 0.116 | 0.130 |

All concentrations are per gram carboxymethycellulose.

The control used in each experiment had all the variables the same except for the concentration of cellulase (1-3 and 7-9 versus 4-6 and 10-12) and concentration of coating agent (1-6 versus 7-12). Each experiment had a cellulase free test to show that any differences in effect was not based solely on diffusion properties.

Turning to the results shown in Table I, there is a clear difference in release characteristics between the control and any of the three concentrations of cellulase, e.g., 2.5 mg, 5.0 mg, and 10 mg/g carboxymethylcellulose. Since there is little difference between the three different concentrations of cellulase, it is apparent that the amount of cellulase needed would be much less than the smallest amount used. In addition, there is little significant effect between using different concentrations of the aluminum cross-linking agent. However, for the smallest concentration of cellulase, it appears that using a smaller amount of cross-linking agent will lead to a faster release rate than is obtained with a larger amount of cross-linking agent. This is an expected result since the more highly cross-linked the vehicle is, the less the cellulase will be able to get into the interstices of the vehicle and catalyze the breakdown of the cellulose. Accordingly, the higher concentrations of cross-linking agents should lead to a slower release rate.

In tests 1-6 versus 7-12, the major variable tested was concentration of the coating agent, hydroxypropylcellulose. The values tested are 6 mg/g CMC and 12 mg/g CMC of hydroxypropylcellulose. Experiments 1-3 have 6 mg hydroxypropylcellulose and no enzyme so act as a control as compared with experiments 4-6 which have the same 6 mg/g hydroxypropylcellulose but have 2.5 mg cellulase/g CMC. As can be seen from Table I, at low concentrations of cross-linking agent, there is significant difference between a release rate from the control and the test sample. Only the highly cross-linked (30 mg/g CMC) tests (experiments 3 and 6) do not follow the same pattern. When the amount of hydroxypropylcellulose is raised to 12 mg/g carboxymethylcellulose, the identical results follow; that is, at low concentrations of cross-linking, there is significant difference in release rate. Only at high concentrations of the cross-linking agent is there no difference. The concentration of coating agent does not seem to be significant.

All the test results are based on the absorbence at 585 nm. Since the cellulase has minimal absorbence at this wavelength, this shows that the differences in absorbence is clearly an effect of the breakdown of the carboxymethylcellulose to release the dye.

Accordingly, it is clear that by varying the concentrations of certain of the factors such as enzyme and cross-linking agent, the controlled properties can be modified.

EXAMPLE 2

In this Example, a large molecule, hemoglobin (molecular weight 68,000 daltons) was used to show the effect of varying concentrations of reactants on the release of the protein. The same procedures were followed to form the test systems as were used in Example 1 except 0.8 mg hemoglobin/g of CMC was used in place of the 0.8 mg Brilliant Blue R/g CMC. Only single concentrations of the cross-linking agent, 20 mg aluminum acetate:borate, the hydrophobicity agent, 40 mg acetic acid/g carboxymethylcellulose, and the coating agent, 18 mg/g CMC hydroxypropylcellulose, were used. The results of this experiment are shown in Table II.

Since hemoglobin was used as the marker, the absorbence at 400 nm was used instead of the 585 nm wavelength used in Example 1. Since cellulase has substantially no absorbence at 400 nm (less than 0.005), any absorbence relates directly to hemoglobin release. As is evident from the results, there is a substantial significant difference between the control and any of the three enzyme tests. This shows that even using 0.025 mg cellulase/g of carboxymethylcellulose, a significant enzyme effect is shown. In fact, there is very little difference in effect with one-hundred fold difference in enzyme concentration.

TABLE II

Concentration effect of cellulase on release of hemoglobin (Hb)
50 mg CMC + Hb, 10 g H$_2$O

| No. | Enzyme (mg/g) | OD/400 nm | | |
|---|---|---|---|---|
| | | 3 hr | 6 hr | 24 hr |
| 1 | 0 | 0.013 | 0.024 | 0.026 |
| 2 | 0.025 | 0.053 | 0.095 | 0.115 |
| 3 | 0.25 | 0.065 | 0.090 | 0.112 |
| 4 | 2.5 | 0.090 | 0.112 | 0.128 |

This experiment clearly shows that a large molecule, e.g., hemoglobin, can be entrapped by the present carboxymethylcellulose system and is released only upon application of the release agent, cellulase.

EXAMPLE 3

In this Example, substantially the same entrapment procedures are used as in Example 2 except an enzyme, glucose oxidase, is entrapped. The purpose of the glucose oxidase test is to show that the entrapped enzyme, glucose oxidase, will retain activity during the entrapment procedure and release from the entrapment vehicle.

The exact procedure is as follows. Approximately 10 g of carboxymethylcellulose (CMC 7H) was mixed with 5 g isopropanol. A NaCl solution (45 mg NaCl/g CMC) containing the enzyme glucose oxidase (2 mg/g CMC) was added over two minutes. The carboxymethylcellulose particles swell, entrapping the enzyme. After ten minutes, the initial solution is decanted and 35 ml of NaCl (45 mg/g CMC) containing a cross-linking agent, aluminum acetate:borate (20 mg/g CMC), and a hydrophobicity agent, acetic acid (40 mg/g CMC) was added. This solution was also added over two minutes. After ten minutes, the solution is decanted and the particles are allowed to air dry overnight.

After drying, the particles were coated with a coating agent and a release agent. Approximately 0.6 ml of isopropanol containing hydroxypropylcellulose (18 mg/g CMC) as a coating agent and differing concentrations of cellulase (see Tables IIIa and IIIb) as a release agent were tested. This isopropanol solution was mixed with one gram of the carboxymethylcellulose containing the glucose oxidase then the resulting particles were dried by forced cool air. In about twenty minutes, the particles were dry.

Release of glucose oxidase from the particles was determined by absorbence measurements. More particularly, 50 mg of each sample was added to 10 g of H$_2$O. The solution was shaken twice, then allowed to incubate for either 2½ hours (Table IIIa) or 4½ hours (Table IIIb). After the incubation period, one gram of the supernatant was added into a solution containing 10 mg of peroxidase (Sigma), 0.9 mg o-Dianisidine DiHCl and 180 mg glucose in 9 g H$_2$O. Absorbence was measured at various times (10, 20, 30, and 45 minutes) as the reaction progressed at 450 nm in a Turner spectrophotometer.

Tables IIIa and IIIb both show that as the level of cellulase is increased, the amount of glucose oxidase released from the particles also increases. Further, as the reaction is allowed to proceed, more glucose is oxidized, showing that the glucose oxidase retains activity. In fact, using the same reagents, 8 μg of glucose oxidase yields an OD of 0.230 after ten minutes and 0.390 after twenty minutes.

TABLE IIIa

Activity studies of Glucose Oxidase after 2½ hours of release from CMC.

| Cellulase (mg/g) | OD 45 nm/Time (Min.) | | | |
|---|---|---|---|---|
| | 10 | 20 | 30 | 45 |
| 0 | 0.008 | 0.009 | 0.012 | 0.016 |
| 0.025 | 0.010 | 0.015 | 0.018 | 0.025 |
| 0.25 | 0.080 | 0.140 | 0.195 | 0.270 |
| 2.5 | 0.110 | 0.200 | 0.280 | 0.395 |

TABLE IIIb

Activity studies of Glucose Oxidase after 4½ hours of release from CMC.

| Cellulase (mg/g) | OD 45 nm/Time (Min.) | | | |
|---|---|---|---|---|
| | 10 | 20 | 30 | 45 |
| 0 | 0.020 | 0.027 | 0.032 | 0.041 |
| 0.025 | 0.042 | 0.068 | 0.086 | 0.115 |
| 0.25 | 0.150 | 0.260 | 0.355 | 0.500 |
| 2.5 | 0.195 | 0.325 | 0.450 | 0.600 |

Those skilled in the art may be able to determine other modifications of the materials and procedures set forth herein. Such other modifications are encompassed by the following claims.

What is claimed is:

1. A system for providing release of an aqueous dispersible entrapped molecule upon hydration comprising:
   an entrapping vehicle formed of a partially cross-linked carboxylated cellulose material, said entrapping vehicle having said molecule entrapped therein,
   a hydroxyalkylcellulose coating agent which forms a barrier around said entrapping vehicle, and
   cellulase, hemicellulase or mixtures thereof as release agent which is quiescent in a dry state but degrades said entrapping vehicle upon hydration to provide release of said entrapped molecule.

2. The system of claim 1 wherein said cellulosic compound is dehydrated.

3. The system of claim 1 wherein said hydroxyalkylcellulose comprises hydroxypropylcellulose.

4. The system of claim 7 wherein said release agent is coated on said entrapping vehicle.

5. The system of claim 7 wherein said release agent is carried by a particle other than said entrapping vehicle, being activated by hydration of said system.

6. The system of claim 5 wherein said particle comprises a dehydrated partially cross-linked carboxylated cellulose material treated with an agent selected from the group consisting of monobasic and dibasic carboxylic acids having 2–6 carbon atoms; salts, chlorides, and anhydrides of said acids; and mixtures thereof.

7. The system of claim 6 wherein said hydrophobicity agent is selected from the group consisting of acetic acid, proprionic acid, butyric, acid, isobutyric acid, succinic acid, adipic acid, phthalic acid, citric acid; salts, chlorides, and anhydrides of said acid; and mixtures thereof.

8. The system of claim 1 wherein said cellulose material is cross-linked by a multivalent metal ion selected from the group consisting of aluminum ions, ferric ions, and mixtures thereof.

9. The system of claim 8 wherein said cellulose material comprises carboxymethylcellulose.

10. The system of claim 9 wherein said carboxymethylcellulose is treated with an agent selected from the group consisting of monobasic and dibasic carboxylic acids having 2-6 carbon atoms; and salts, chlorides, and anhydrides of said acids; and mixtures thereof.

11. The system of claim 10 wherein said agent is selected from the group consisting of acetic acid, proprionic acid, butyric acid, isobutyric acid, succinic acid, adipic acid, phthalic acid, citric acid; salts, chlorides, and anhydrides of said acid; and mixtures thereof.

12. A method of making a cellulose-based system for entrapping and releasing an aqueous dispersible molecule comprising the steps of:

soaking a carboxylated cellulosic material in an aqueous solution of the molecule to be entrapped, treating said soaked material with a cross-linking agent to produce a cellulose material containing an entrapped molecule, and adding cellulase, hemicellulase or a mixture thereof as a release agent to said treated material, said release agent being quiescent in a dry state but capable of degrading said treated material upon hydration, and having hydroxyalkylcellulose as a coating agent.

13. The method of claim 12 wherein said treatment step further comprises treating with an agent selected from the group consisting of monobasic and dibasic carboxylic acids having 2-6 carbon atoms; salts, chlorides, and anhydrides of said acids; and mixtures thereof.

14. The method of claim 13 wherein said hydrophobicity agent is selected from the group consisting of acetic acid, proprionic acid, butyric acid, isobutyric acid, succinic acid, adipic acid, phthalic acid, citric acid; salts, chlorides, and anhydrides of said acid; and mixtures thereof.

15. The method of claim 12 wherein said treated material is dried before adding said release agent.

16. The method of claim 12 wherein said release agent is coated on said treated material together with said coating agent.

17. The method of claim 12 wherein said cross-linking agent is selected from the group consisting of aluminum ions, ferric ions, and mixtures thereof.

18. The method of claim 12 wherein said cellulose material comprises carboxymethylcellulose.

19. The method of claim 18 wherein said carboxymethylcellulose has a DS of at least 0.5.

* * * * *

UNITED STATES PATENT AND TRADEMARK OFFICE
CERTIFICATE OF CORRECTION

PATENT NO. : 5,049,395
DATED : September 17, 1991
INVENTOR(S) : An-Cheng Chang et al.

It is certified that error appears in the above-identified patent and that said Letters Patent is hereby corrected as shown below:

On the title page, item [75], add

— Donald F.H. Wallach, Hollis, N.H.—.

Column 5, lines 20, replace "containiing" with --containing--.

Column 5, line 20, replace "hydroxypropylcellulose coating agent" with --hydroxylpropylcellulose as a coating agent--.

Column 5, line 24, replace "(see Table I) The" with --(see Table I). The".

UNITED STATES PATENT AND TRADEMARK OFFICE
CERTIFICATE OF CORRECTION

PATENT NO. : 5,049,395

DATED : September 17, 1991

INVENTOR(S) : An-Cheng Chang et al.

It is certified that error appears in the above-indentified patent and that said Letters Patent is hereby corrected as shown below:

Column 5, line 65, replace "cellulase free" with --cellulase-free--.

Signed and Sealed this

Second Day of November, 1993

Attest:

BRUCE LEHMAN

Attesting Officer

Commissioner of Patents and Trademarks